United States Patent [19]

Kruse

[11] 4,029,878

[45] June 14, 1977

[54] PROCESS FOR PREPARING MANNITOL FROM GLUCOSE

[75] Inventor: Walter M. Kruse, Wilmington, Del.

[73] Assignee: ICI United States Inc., Wilmington, Del.

[22] Filed: May 19, 1975

[21] Appl. No.: 578,548

[52] U.S. Cl. .............................. 536/1; 260/635 C
[51] Int. Cl.² ........................................ C07H 1/00
[58] Field of Search ................. 260/209 R, 635 C; 536/1

[56] References Cited

UNITED STATES PATENTS

| | | | |
|---|---|---|---|
| 1,990,245 | 2/1935 | Mueller et al. | 260/635 C |
| 2,280,975 | 4/1942 | Power | 260/635 C |
| 2,642,462 | 6/1953 | Kasehagen | 260/635 C |
| 2,759,023 | 8/1956 | Kool et al. | 260/635 C |

OTHER PUBLICATIONS

Bilik, "Chem. Zvesti" 26, pp. 183–186, 1972.

Primary Examiner—Johnnie R. Brown

[57] ABSTRACT

Mannose is produced from a concentrated solution of glucose or polymers of glucose in the presence of a catalyst containing hexavalent molybdenum. Subsequent hydrogenation of the product in order to produce mannitol is also disclosed.

18 Claims, No Drawings

PROCESS FOR PREPARING MANNITOL FROM GLUCOSE

BACKGROUND OF THE INVENTION

This invention relates to processes for preparing mannitol. More particularly, this invention relates to processes for preparing mannitol by catalytic isomerization of glucose to procedure a mixture of glucose and mannose, followed by catalytic hydrogenation of the isomerizate.

It is well known that a mixture of sorbitol and mannitol in aqueous solution can be produced by catalytic hydrogenation of invert sugar, which is an approximately equimolar mixture of glucose and fructose. Invert sugar, in turn, is commonly obtained by inversion of sucrose. Processes for hydrogenation of invert sugar are disclosed, for example, in U.S. Pat. Nos. 2,759,024; 3,329,729; 3,705,199; and 3,763,246. The yield of mannitol is ordinarily about 24–26 percent by weight, based on total dry solids; this yield can be increased to about 30 percent by weight by appropriate choice of catalyst, as described in U.S. Pat. Nos. 3,705,199 and 3,736,246 cited supra. Mannitol is readily recovered from aqueous solutions containing both sorbitol and mannitol by fractional crystallization, as described for example in U.S. Pat. No. 3,632,656. Hydrogenation of invert sugar is an attractive commercial route to the production of mannitol when the price of sucrose (ordinary sugar) is low. However, recent sharp rises and fluctuations in the price of sucrose have indicated a need for alternate routes.

It is also known that glucose can be isomerized under alkaline conditions to yield a mixture containing glucose, fructose, and mannose. Various alkaline materials for this purpose, including sodium hydroxide and calcium hydroxide, are known. The proportions of glucose, fructose, and mannose in the reaction mixture will vary depending on the alkaline material and the conditions used, and significant quantities of mannose are not always obtained. References describing the alkaline isomerization of glucose include U.S. Pat. No. 3,256,270 and W. Pigman, "The Carbohydrates: Chemistry, Biochemistry, and Physiology", Academic Press, New York, 1957, pages 60–69.

It is also known that both D-glucose and D-mannose can be epimerized in an aqueous solution containing about 17% by weight of D-glucose or D-mannose, based on total solution weight (i.e., 20% by weight of glucose, based on the weight of water) and a small amount of molybdic acid catalyst producing a solution containing 25 percent D-mannose, remainder D-glucose on the dry basis. This epimerization is described by V. Bilik, Chem. Zvesti, 26, 183–186 (1972) and in Czech patent 149,051 (June 15, 1973). No reaction took place when sodium molybdate was used as the catalyst. Bilik and co-workers have also found that various other sugars can be epimerized in the presence of molybdate ions in aqueous solution. For example, D-fructose gives a mixture of D-sorbose, D-tagatose, and D-psicose, and sucrose gives a mixture of D-mannose and D-sorbose in a similar reaction. [Chemical Abstracts, 80, 146433s (1974)]. Also, L-arabinose gives a mixture of L-arabinose and L-ribose [Czechoslovakian Patent 149,472, July 15, 1973; C.A. 81, 78189k (1974)]; L-mannose gives a mixture of L-glucose and L-mannose [C.A. 81, 91887f (1974)]; and D-galactose gives a mixture of D-talose and D-gulose in addition to D-galactose [C.A. 81, 152523h (1974)].

SUMMARY

It has been found according to the present invention that an enhanced yield of mannose is obtained by using as the starting material a solution containing glucose in a concentration of at least about 50 percent by weight. This invention comprises contacting a solution containing at least about 50 percent by weight of glucose or polymer thereof (including mixtures of glucose and polymer thereof) with a catalyst containing molybdenum in the hexavalent state at a temperature of at least about 70° C. A solution containing glucose and mannose is obtained. This solution can be catalytically hydrogenated to produce a solution containing sorbitol and mannitol, from which mannitol can be recovered by fractional crystallization.

DESCRIPTION OF PREFERRED EMBODIMENT

Applicant has made the surprising discovery that the yield of mannose obtained by catalytic epimerization of glucose using a hexavalent molybdenum catalyst is significantly increased when the concentration of glucose in the starting solution is at least about 50 percent by weight, based on total solution weight. Glucose concentrations of about 67 percent to about 70 percent by weight are preferred. Solubility problems are encountered at glucose concentrations substantially above 70 percent. By way of example, yields of about 30–33 percent of mannose are obtained at equilibrium when an aqueous solution containing 67 percent by weight of glucose is epimerized at a temperature of about 90° C., contrasted with mannose yields of about 25 percent as reported by Bilik in Chem. Zvesti, 26, 183–186 (1972) cited supra when an aqueous solution containing 17 percent by weight glucose is epimerized using the same catalyst and conditions. This finding is surprising because ordinarily the equilibrium concentration of sugars obtained by epimerization varies little or not at all with the sugar concentration in the starting solution. The ratio of mannose to glucose obtained in the present process is nearly ½, contrasted with ⅓ in the work done by Bilik. Since the mannitol/sorbitol ratio obtained after catalytic hydrogenation is very nearly the same as the mannose/glucose ratio, it is evident that the increase in mannose yield obtained by applicants results in substantially increased mannitol recovery and a much higher ratio of desired mannitol to by-product sorbitol.

The term "glucose" refers to D-glucose, and the term "mannose" refers to D-mannose throughout the specification.

The starting carbohydrate used in this invention is glucose, a polymer of glucose, or a mixture of glucose and polymers thereof. Glucose is the preferred carbohydrate, and the description herein will be directed primarily to processes using glucose as the starting material.

The carbohydrate is dissolved in an inert solvent to give a concentration of at least about 50 percent by weight of carbohydrate. Water is by far the preferred solvent because it gives excellent results and has a much lower cost than other solvents. However, various inert polar organics solvents, such as dimethyl acetamide (DMA) and dimethyl sulfoxide (DMSO) can be used with good results.

When water is used as the solvent, it is essential to use an acidic solution. The preferred pH of an aqueous solution used in this invention is from about 3 to about 5. When the pH of the starting solution is below 3, the starting carbohydrate undergoes a number of undesirable side reactions. When the pH is above 5, yields of mannose decrease. At a pH greater than 7, practically no mannose is produced.

Epimerization according to this invention is carried out in the presence of a catalyst comprising molybdenum in the hexavalent state, such as molybdic acid, isopolymolybdic acids, heteropolymolybdic acids and acid salts such as sodium phosphomolybdate, and silicomolybdic acid, or an anion exchange resin in which the hydroxyl ions have been replaced by molybdate ions. Molybdenyl bis-acetylacetonate has been found to be a good catalyst in non-aqueous media such as dimethylacetamide and dimethylsulfoside. Sodium molybdate is not a suitable catalyst unless sufficient acid to give an acidic pH, preferably in the range of about 3 to 5, is also present. Pentavalent molybdenum has been found not to have catalytic activity for epimerization, although it appears that mixtures of pentavalent and hexavalent molybdenum have catalytic activity. It is known that molybdic acid forms low molecular weight polymers or oligomers in acidic solution, and the term "molybdic acid" herein includes such polymers and oligomers.

The catalyst can be added to the reaction medium either before, with, or after addition of the glucose.

The concentration of catalyst should be at least about 0.05 percent by weight, based on the weight of carbohydrate. At least 0.1 percent by weight of catalyst should be used at temperatures below 110° C. Higher catalyst concentrations, for example about 0.25 to about 1 percent by weight are ordinarily preferred. As the concentration of catalyst increases from 0.1 percent to 1 percent, the reaction time is decreased. Catalyst concentrations above about 1 percent do not noticably decrease reaction time, while concentrations below about 0.05 percent are too low to give effective conversion of glucose to mannose.

The reaction temperature for epimerization of glucose is at least about 70° C. The preferred temperature range is from about 85° C. to about 160° C., and temperatures of about 100° C. to about 125° C. are especially preferred. At temperatures below 70° C., reaction takes place very slowly and good yields of mannose are not obtained. The reaction becomes progressively faster as the temperature is increase. The reaction rate reaches an optimum at temperatures above 100° C. Epimerization products of excellent purity, containing no more than about 1.5 percent by weight of impurities on the dry basis, are obtained at temperatures up to about 125° C or slightly higher. Less than 2 percent of impurities are obtained at 130° C. Production of impurities gradually increases as the reaction temperature is increased above about 125° C. Caramelization of glucose tends to occur at temperatures above about 160° C.

Pressure appears to have little effect on the course of the epimerization reactions; for reasons of economy atmospheric pressure is preferred.

The time required for epimerization depends upon the temperature and the catalyst concentration as discussed above. Ordinarily, the desired yields of glucose are obtained in about 30 to about 120 minutes, although in some cases shorter times may be used, particularly at temperatures near the upper end of the preferred range, and in other cases, for example when a low catalyst concentration is used, a longer time may be necessary. The epimerization reaction is an equilibrium reaction; hence the yield of mannose reaches a maximum when equilibrium is reached and does not change thereafter.

Starting materials containing glucose polymers can be used, although yields of mannose tend to be lower than those obtained with glucose as the starting material. The suitable glucose polymer-containing starting materials are those in which the polymer content is readily hydrolyzable to glucose under mildly acidic conditions, these materials by and large are those in which the polymer content is in the form of low molecular weight polymers (typically 10 glucose units or less) which are commonly known as oligomers. Maltose, which is a dimer of glucose, is a suitable starting material. Of more interest from an economic standpoint are starch hydrolyzates such as cornstarch hydrolyzate, which consists essentially of glucose and oligomers thereof and which is obtained as a by-product from the hydrolysis of cornstarch. A typical composition of cornstarch hydrolyzate is approximately 63 percent by weight of glucose and 37 percent by weight of glucose oligomers on the dry basis. Cornstarch hydrolyzate is much less expensive than glucose. The concentration of cornstarch hydrolyzate (or other glucose polymer-containing starting material) used in the present process is about the same as the glucose concentrations previously stated, i.e., at least about 50% by weight and preferably about 67–70% by weight of carbohydrate. Water is the preferred solvent.

The reaction of oligomer-containing materials such as cornstarch hydrolyzate is actually a combined hydrolysis and epimerization, with both probably taking place simultaneously. The preferred pH range (about 3 to 5) for epimerization is also excellent for hydrolysis of oligomers. Preferred temperatures for the combined hydrolysis and epimerization of cornstarch hydrolyzate are from about 125° to about 160° C. Hydrolysis of oligomers is unduly slow at temperatures below 125° C., while relatively large amounts of impurities are formed at temperatures above 160° C. Reaction times for cornstarch hydrolyzate are generally longer than those required for glucose. Hydrolysis and epimerization are preferably carried out as a single step, although the cornstarch hydrolyzate can be partially hydrolyzed in a separate step prior to epimerization if desired.

The present process has at least two major advantages over the process of Bilik in which a comparatively dilute solution of glucose is epimerized. First, the yield of mannose is unexpectedly higher in more concentrated solutions as previously mentioned. Secondly, it is not necessary to evaporate large quantities of water during the course of the present process, since the solution of glucose and mannose obtained on epimerization is sufficiently concentrated for subsequent hydrogenation and product recovery. If the comparatively dilute glucose-mannose solution obtained by Bilik were used for mannitol production, it would be necessary to evaporate large quantities of water either before or after the hydrogenation step in order to recover the mannitol product.

The epimerization process may be carried out as a batch, semi-continuous, or continuous operation. Any suitable equipment that allows intimate contact of the reactant and catalyst may be used.

When the epimerization reaction is complete, the molybdenum catalyst may be removed from the solution, preferably by diluting the solution with water to about 50% solids and adding either a mixed ion exchange resin (a mixture of an anion exchange resin and a cation exchange resin) or activated charcoal, or both. Dilution is necessary because the ion exchange resin does not perform efficiently at the solids concentrations (ordinarily about 67–70%) used for epimerization. Activated charcoal also removes trace impurities if present. The precipitated catalyst is then removed from the slurry, preferably by filtration.

The product from the epimerization process can then be catalytically hydrogenated to produce a solution of sorbitol and mannitol by methods known in the art. Supported nickel and supported ruthenium catalysts are ordinarily preferred. For example, the hydrogenation step can be carried out using a supported nickel catalyst such as nickel on kieselguhr as described in U.S. Pat. No. 2,518,235, or the supported phosphated nickel catalyst described in U.S. Pat. Nos. 3,538,019 and 3,670,035. Other nickel catalysts are also known in the art. Alternatively, a supported ruthenium catalyst, such as ruthenium on charcoal as described in U.S. Pat. No. 2,868,847, or ruthenium supported on an aluminosilicate clay of the montmorillonite type, as disclosed in copending U.S. patent application Ser. No. 531,972, filed Dec. 12, 1974, now U.S. Pat. No. 3,963,789 issued June 15, 1976, can be used.

When a nickel hydrogenation catalyst is used, the epimerization product solution can be hydrogenated directly provided a comparatively low molybdenum catalyst concentration (about 0.125% by weight or less, based on carbohydrate) is used. Higher molybdenum catalyst concentrations (about 0.25% or greater) appear to slow the hydrogenation rate, so that at least partial removal of the molybdenum catalyst prior to hydrogenation is indicated. When a ruthenium hydrogenation catalyst is used, all or most of the molybdenum catalyst must be removed prior to hydrogenation, since molybdenum appears to poison the ruthenium catalyst. Molybdenum removal can be carried out as above described, i.e., by diluting the epimerization product solution, removing the molybdenum with an ion exchange resin and/or carbon, and then concentrating the solution (e.g., by evaporation of water) to the level (ordinarily about 70% solids) desired for hydrogenation. Removal of molybdenum at this stage is costly, because a costly evaporation step is required. This represents a distinct advantage for the nickel catalyst.

The solution of glucose and mannose from the epimerization step, and the catalyst, are placed in an autoclave which has been purged of air, and the autoclave contents are catalytically hydrogenated at a temperature which is ordinarily about 100°–160° C. (although slightly higher temperatures not exceeding 200° C. can be used) and at a pressure of at least about 1,000 psig., typically about 1500–2200 psig. The concentration of the solution during hydrogenation is not critical, but ordinarily a comparatively concentrated solution (e.g., about 70% solids) is preferred in order to minimize the quantity of fluid handled and to simplify subsequent product recovery. Reaction is continued until the pressure remains constant. Ordinarily no more than about ½ hour to about 1 hour is required for hydrogenation. Since the carbohydrate content of the isomerizate obtained from the first reaction step is entirely or almost entirely in the form of monosaccharides, even when cornstarch hydrolyzate or other glucose polymer-containing starting material is used, comparatively short reaction times and low temperatures as indicated can be used in the hydrogenation step. Hydrogenation yields a solution of sorbitol and mannitol in about the same proportions as those of glucose and mannose in the isomerizate, i.e., typically about 30–33 percent mannitol the rest sorbitol on the dry basis. The solution also contains water or other solvent. Mannitol may be recovered by means known in the art, e.g., by fractional crystallization.

This invention will now be described in further detail with reference to the following examples. In the examples, the concentrations of glucose are given in percent by weight, based on total solution weight; amounts of molybdenum catalyst are given in percent by weight, based on the weight of glucose (or cornstarch hydrolyzate); mannose determinations are made by TLC and are given in percent by weight, based on the total weight of sugar solids; and mannitol and sorbitol determinations are made by GLC (gas-liquid chromatography) and are given in percent by weight on the dry basis.

EXAMPLE 1

An aqueous solution of 70 percent by weight of glucose is prepared by adding 120 g. of glucose to distilled water in a 180 ml. pop bottle at atmospheric pressure and room temperature (about 25° C.). To this is added .30 g. of molybdic acid (0.25% by weight). The pH is found to be about 4. The bottle is stoppered and the solution is magnetically stirred in a constant temperature bath at 120° C for 30 minutes. The reaction is carried out at ambient pressure, i.e., the pressure which develops as a result of heating the closed bottle and its contents. The bottle is then removed from the constant temperature bath and allowed to cool. About 30 g. of mixed bed ion exchange resin (a combination of a cation exchange resin and an anion exchange resin) and enough water to dilute the solution to about 50% sugar concentration are then added, and the solution is filtered.

Analysis of the filtrate (by TLC) shows that the mixture contains 33.3% by weight of mannose.

EXAMPLES 2–16

The process of Example 1 is repeated, varying the temperature, reaction time, and the concentration of the molybdic acid as shown in Table I below. The concentration of glucose in all of these examples is from 67% to 70% by weight, based on the total weight of solution. In general 100 g. of glucose is used. All runs are carried out at ambient pressure.

The resulting percentages of mannose appear in Table I.

TABLE I

| Example No. | Temp ° C. | Time min. | Conc. of Molybdic acid | Mannose product wt % |
| --- | --- | --- | --- | --- |
| 2 | 75° | 420 | 1% | 33.8% |
| 3 | 80.5° | 360 | 0.25% | 23.3% |
| 4 | 80.5° | 1020 | 0.25% | 22.2% |
| 5 | 90° | 60 | 1% | 32.4% |
| 6 | 90° | 300 | 0.5% | 33.6% |
| 7 | 90° | 120 | 0.25% | 20.2% |
| 8 | 90° | 380 | 0.25% | 33.0% |
| 9 | 90° | 120 | 0.125% | 21.1% |
| 10 | 90° | 420 | 0.125% | 21.9% |
| 11 | 90° | 703 | 0.125% | 30.7% |
| 12 | 110° | 30 | 0.25% | 29.6% |

TABLE I-continued

| Example No. | Temp °C. | Time min. | Conc. of Molybdic acid | Mannose product wt % |
|---|---|---|---|---|
| 13 | 110° | 60 | 0.25% | 31.8% |
| 14 | 110° | 90 | 0.25% | 31.0% |
| 15 | 130° | 30 | 0.125% | 33.4% |
| 16 | 130° | 40 | 0.25% | 33.7% |

As may be seen from Table I, the reaction time required tends to decrease as temperature and catalyst concentration are increased. Temperatures above about 85° C. are preferred because lower temperatures, while operative, require longer reaction times.

EXAMPLE 17

The process of Example 1 is repeated, except that the catalyst is 1% by weight of sodium phosphomolybdate, based on the weight of glucose, the reaction medium has a pH of 4, and the reaction time is 180 minutes. The temperature is 90° C. and the glucose concentration is 67%. A reaction product containing 33.7% mannose is obtained.

EXAMPLE 18

The process in Example 1 is repeated, with the following exceptions: 1 g. of $H_2MoO_4$ on 5 g. of "Amberlyst A-26" styrene-divinyl benzene quaternary anion exchange resin (obtained from Rohm and Haas Company, Philadelphia, Pa.) is used instead of molybdic acid; the temperature is 90° C.; the reaction time is 180 minutes; and the concentration of glucose is 50% by weight. The product contains 23.0% by weight of mannose.

EXAMPLE 19

The procedure of Example 18 is repeated except that the starting glucose concentration is 55% and a catalyst containing 2 g. of $H_2MoO_4$ on 12.5 g. of "A-26" resin is used. The product contains 29.7% by weight of mannose.

EXAMPLE 20

The procedure of Example 1 is repeated except that the catalyst is 0.25% of molybdenum (VI) cobaltate, and the reaction time is 75 minutes and the reaction temperature is 120° C. Analysis of the product (by TLC) show 38% of mannose.

EXAMPLE 21

A solution containing 2 g. of glucose and 40 mg. of molybdenyl bis-acetylacetonate in 5 ml. of dimethylacetamide, is heated to 100° C. and maintained at this temperature for 2 hours. Analysis of the reaction product after cooling shows 42.4% by weight of mannose, based on the combined weights of mannose and glucose.

EXAMPLE 22

A solution containing 4 g. of glucose and 40 mg. of molybdenyl bis-acetylacetonate in 8 ml. of dimethyl sulfoxide is heated to 90° C. and maintained at this temperature for 2 hours. Analysis of the reaction product after cooling shows 32.1% by weight of mannose, based on the combined weights of mannose and glucose.

The following examples describe the production of mannitol from glucose.

EXAMPLE 23

An aqueous solution containing 67% by weight of glucose and 0.5% by weight of molybdic acid, based on the weight of glucose, is epimerized according to the procedure of Example 6 (i.e., at 90° C for 300 minutes). The reaction product after dilution to 50% solids is treated with a mixed bed ion exchange resin as described in Example 1, and then with decolorizing charcoal, both of which are removed by filtration. The filtrate contains 33.6% by weight of mannose, based on the weight of sugar solids.

Three grams of catalyst consisting of 1% by weight of ruthenium supported on an acid treated montmorillonite clay, are added to the above filtrate, which contains 100 g. of sugar solids. The montmorillonite clay support, which is sold under the designation "K-10" by Chemetron Corporation, is a powder which typically contains about 64.7% by weight silica and 19.3% by weight alumina, and which typically has a pH of about 3.5 in a 1:10 (by weight) clay/water slurry, a bulk density of about 373 g/liter, a specific gravity of about 2.4–2.5, and a surface area of 268 m2/g. The resulting slurry is charged to a one-liter stainless steel autoclave equipped with a temperature controller and a two-pen temperature and pressure recorder. The autoclave is purged with nitrogen and hydrogen, and the pressure is raised to 1550 psig. hydrogen pressure. The slurry is then heated to 160° C. with constant stirring. The reaction is allowed to continue at 160° C. for 50 minutes, and then the autoclave is cooled to room temperature. The reaction product is analyzed by GLC (gasliquid chrometography). A product containing 27.0% by weight of mannitol and 72.0% by weight of sorbitol on the dry basis is obtained.

EXAMPLES 24–27

The procedure of Example 23 is repeated except that epimerization catalysts, catalyst concentrations, and reaction conditions are as shown in Table II below. Hydrogenation catalyst and conditions are the same as in Example 23. The epimerization procedures in Examples 24 and 25 are the same as in Examples 17 and 18, respectively. Analyses for mannose, mannitol, and sorbitol are given in Table II.

TABLE II

|  | Ex. 24 | Ex. 25 | Ex. 26 | Ex. 27 |
|---|---|---|---|---|
| Epimerization: |  |  |  |  |
| Catalyst | D | C | A | B |
| % catalyst | 1% | 2% | 0.125% | 0.125% |
| Temp., °C. | 90 | 90 | 130 | 110 |
| Time, min. | 180 | 180 | 30 | 120 |
| pH | 4 | 4 | 4 | 3.2 |
| % mannose | 33.7 | 29.7 |  |  |
| Hydrogenation: |  |  |  |  |
| % mannitol | 29.9 | 29.7 | 31 | 31.3 |
| % sorbitol | 67.9 | 68.5 |  |  |
| Catalysts: |  |  |  |  |
| A — $H_2MoO_4$ |  |  |  |  |
| B — $H_2MoO_4$ + $H_3PO_4$ |  |  |  |  |
| C — $H_2MoO_4$ on "A-26" anion exchange resin |  |  |  |  |
| D — Sodium phosphomolybdate |  |  |  |  |

EXAMPLES 28–30

The procedure of Example 23 is repeated with the following exceptions: (1) the hydrogenation catalyst is nickel on kieselguhr, containing about 20% by weight Ni, (2) no analysis of the epimerizate for mannose is made, and (3) amounts of epimerization catalyst (molybdic acid) and reaction conditions for each step are shown in Table III below. Amounts of mannitol in the final product are also given in Table III.

TABLE III

|  | Ex. 28 | Ex. 29 | Ex. 30 |
|---|---|---|---|
| Epimerization: |  |  |  |
| % catalyst | 0.25% | 0.25% | 0.125% |
| Temp., °C. | 90 | 110 | 120 |
| Time, min. | 390 | 80 | 60 |
| pH | 4 | 4 | 4 |
| Hydrogenation: |  |  |  |
| Temp. °C. | 160 | 160 | 160 |
| Time, min | 60 | 60 | 60 |
| % mannitol | 27.5 | 30.8 | 31.3 |
| % sorbitol | 72.5 | 69.2 | 68.7 |

EXAMPLE 31

An aqueous solution containing 70% by weight of glucose and 0.125% by weight of molybdic acid, based on the weight of glucose, is epimerized at 120° C. and ambient pressure for one hour in a stoppered bottle. The resulting solution after cooling to room temperature, and 3% by weight, based on initial glucose weight, of nickel on kieselguhr catalyst containing 20% by weight Ni are charged to an autoclave at 30° C. The autoclave is pressured with hydrogen to 1560 psig., and the autoclave contents are then heated to 150° C. and resulting pressure (2020 psig.) and maintained at 150° C. for 90 minutes. The autoclave contents are then cooled to room temperatures and the nickel catalyst is separated by filtration. The pH of the solution is 5.0. A sample of the filtrate is found to contain 1.3 ppm of Mo, based on total solution weight. The filtrate is then treated with a mixed bed ion exchange resin (a cation exchange resin and an anion exchange resin). Analysis of the ion exchange solution shows the following: mannitol, 33.1%, reducing sugar, 0.76%, total sugar, 1.4%. All percentages are by weight on the dry basis. The low amount of Mo in the filtrate indicates that most of the molybdenum is deposited on the nickel catalyst support. The valence state of the molybdenum was not determined.

This example shows that the molybdenum catalyst used for epimerization does not interfere with the nickel hydrogenation catalyst. Therefore it is possible to hydrogenate an epimerizate directly without separation of the molybdenum catalyst and without dilution, as was done here. When ruthenium is used as the hydrogenation catalyst, it is necessary to remove the molybdenum catalyst prior to hydrogenation, as indicated in other experiments.

An attempt to epimerize and hydrogenate simultaneously a 70% aqueous solution of glucose resulted in the formation of very little mannitol.

EXAMPLE 32

The procedure of Example 31 is repeated except that (a) the molybdic acid concentration is 0.07%, based on glucose, and (b) the hydrogenation time is 60 minutes. The solution after hydrogenation has a pH of 4.7. The product contains 33.6% mannitol, 0.44% reducing sugar and 1.4% total sugar on the dry basis.

This example shows that low molybdenum catalyst concentrations, in this case 0.07% can be used.

EXAMPLES 33–36

These examples describe the simultaneous hydrolysis and epimerization of cornstarch hydrolyzate, a commercial by-product obtained from cornstarch hydrolysis and containing about 63% glucose and 37% higher polysaccharides (mostly oligomers containing 2 to 6 glucose units), and the subsequent catalytic hydrogenation of the epimerization reaction product to form a product containing mannitol and sorbitol.

The epimerization catalyst is $H_2MoO_4$ on an anion exchange resin (as described in Example 18) in Examples 33, 34 and 35, and is molybdic acid in Example 36.

A 1% ruthenium on montmorillonite hydrogenation catalyst as described in Example 23 is used in all four examples. Hydrogenation is carried out first at 160° C., followed by a further period at 175° C.

The manipulative steps, except as noted above, are carried out as in Example 23. Amounts of catalyst, reaction conditions and product analyses are given in Table IV below.

TABLE IV

|  | Ex. 33 | Ex. 34 | Ex. 35 | Ex. 36 |
|---|---|---|---|---|
| Epimerization |  |  |  |  |
| Catalyst | C | C | A | C |
| % catalyst | 1% | 2% | 1% | 1% |
| Time, min. | 180 | 180 | 180 | 240 |
| Temp., °C. | 95 | 95 | 90 | 92 |
| pH | 4 | 4 | 4 | 4 |
| Sugar conc. | 50 | 50 | 66.7 | 66.7 |
| Mannose | 21.2 | 22.0 |  |  |
| Hydrogenation |  |  |  |  |
| Min. at 160° C. | 30 | 45 | 55 | 50 |
| Min. at 175° C. | 60 | 45 | 30 | 30 |
| Mannitol | 18.5 | 23.4 | 19.5 | 19.9 |
| Sorbitol | 78.1 | 73.4 | 64.4 | 77.3 |

A — $H_2MoO_4$
C — $H_2MoO_4$ on "A-26" anion exchange resin

The low yields of mannose and mannitol from cornstarch hydrolyzate, as shown in Table IV, compared to yields obtained from glucose, are attributable at least in part to the use of epimerization temperatures which are too low for efficient hydrolysis of oligosaccharides to glucose. However, it is probable that yields of mannose from cornstarch hydrolyzate will be somewhat lower than yields from glucose, even when the epimerization temperature is optimized.

COMPARATIVE EXAMPLES A–D

Aqueous solutions containing 20% by weight of glucose and 1% by weight of molybdic acid, based on the weight of glucose, and having a pH of 4, are epimerized at 90° C. Reaction times, which are different in each example, are given in Table V below. The reaction product mixtures are allowed to cool, the molybdenum, catalyst is separated from the reaction product solution as described in Example 1, and the filtrate was analyzed for mannose (in percent by weight of total sugar solids) by TLC. Results are given in Table V below.

TABLE V

| Example | Time, min. | Wt. % Mannose |
|---|---|---|
| A | 60 | 26.5 |
| B | 120 | 26.2 |
| C | 180 | 27.3 |
| D | 360 | 24.6 |

The mannose yields obtained in these examples are about the same as those obtained by Bilik and are significantly lower than those obtained upon epimerization of solutions containing 67–70 percent by weight of glucose at the same temperature and catalyst concentration.

What is claimed is:

1. In a process for producing a solution containing glucose and mannose by contacting an acidic solution of glucose, oligomers of glucose, or a mixture of glucose and oligomers thereof, with a catalyst containing molybdenum in the hexavalent state at a temperature of at least about 70° C. under non-hydrogenating conditions, the improvement wherein said solution has a carbohydrate content of at least about 50 percent by weight.

2. A process according to claim 1 in which the solution is an aqueous solution.

3. A process according to claim 2, in which the pH of the solution is from about 3 to about 5.

4. A process according to claim 1 in which the solvent is a polar organic solvent.

5. A process according to claim 1 in which glucose is the starting material.

6. A process according to claim 1 in which the starting material is a carbohydrate consisting essentially of glucose and oligomers thereof.

7. A process according to claim 6 in which the starting material is cornstarch hydrolyzate.

8. A process according to claim 1 in which the reaction temperature is in the range of about 85° to about 160° C.

9. A process according to claim 1 in which the amount of catalyst is at least about 0.05% by weight, based on the weight of carbohydrate.

10. A process according to claim 1, in which the catalyst is molybdic acid.

11. A process according to claim 1, in which catalyst is an alkali metal phosphomolybdate.

12. A process according to claim 1, in which the catalyst comprises molybdenum on an ion-exchange resin.

13. A process according to claim 1 comprising the further step of removing of the molybdenum catalyst from the solution of glucose and mannose.

14. A process according to claim 1 including the further steps of hydrogenating said solution of glucose and mannose at an elevated temperature in the presence of an hydrogenation catalyst, thereby producing a solution containing sorbitol and mannitol, and recovering mannitol from said solution.

15. A process according to claim 14 in which the solution is an aqueous solution.

16. A process according to claim 14 in which the hydrogenation catalyst is a nickel catalyst.

17. A process according to claim 16 in which said solution of glucose and mannose is hydrogenated without prior removal of said molybdenum catalyst.

18. A process according to claim 14 in which the hydrogenation catalyst is a ruthenium catalyst and in which the molybdenum catalyst is separated from the solution of glucose and mannose prior to hydrogenation.

* * * * *